(12) United States Patent
Tiwari et al.

(10) Patent No.: US 10,047,134 B2
(45) Date of Patent: Aug. 14, 2018

(54) **PROCESS FOR EXPRESSION OF RECOMBINANT PROTEINS IN *PICHIA PASTORIS* USING A FED BATCH MODEL**

(71) Applicant: Biocon Limited, Bangalore (IN)

(72) Inventors: Sanjay Tiwari, Bangalore (IN); Gourav Awasthi, Pradesh (IN); Gokul Jothiraman, Nadu (IN); Arun Chandavarkar, Bangalore (IN)

(73) Assignee: Biocon Limited, Bangalore (IN)

( * ) Notice: Subject to any disclaimer, the term of this patent is extended or adjusted under 35 U.S.C. 154(b) by 310 days.

(21) Appl. No.: 14/760,123

(22) PCT Filed: Jan. 10, 2014

(86) PCT No.: PCT/IB2014/058171
§ 371 (c)(1),
(2) Date: Jul. 9, 2015

(87) PCT Pub. No.: WO2014/108856
PCT Pub. Date: Jul. 17, 2014

(65) Prior Publication Data
US 2015/0353620 A1    Dec. 10, 2015

(30) Foreign Application Priority Data

Jan. 10, 2013  (IN) ............................ 137/CHE/2013

(51) Int. Cl.

| | |
|---|---|
| *C12N 15/81* | (2006.01) |
| *C12R 1/84* | (2006.01) |
| *C12N 15/11* | (2006.01) |
| *C12N 1/16* | (2006.01) |
| *C07K 14/62* | (2006.01) |
| *C12P 21/00* | (2006.01) |
| *C12N 9/48* | (2006.01) |
| *C12P 1/02* | (2006.01) |
| *A61K 38/00* | (2006.01) |

(52) U.S. Cl.
CPC ................ *C07K 14/62* (2013.01); *C12N 1/16* (2013.01); *C12N 9/485* (2013.01); *C12P 1/02* (2013.01); *C12P 21/00* (2013.01); *C12Y 304/17002* (2013.01)

(58) Field of Classification Search
None
See application file for complete search history.

(56) References Cited

U.S. PATENT DOCUMENTS 5,672,496 A * 9/1997 Fayerman ............... C12N 9/48
435/212
2008/0300183 A1* 12/2008 Boyle ............... A01K 67/0275
514/8.9
2012/0295307 A1* 11/2012 Monod ................... C12N 9/60
435/69.1
2015/0118710 A1* 4/2015 Govindappa .. C12Y 304/21061
435/69.4
2015/0252321 A1* 9/2015 Roy ...................... C12N 5/0031
435/350

FOREIGN PATENT DOCUMENTS

WO    WO-03106690 A1    12/2003

OTHER PUBLICATIONS

Zhang at I. (2000) Fermentation Strategies for Recombinant Protein Expression in the Methylotrophic Yeast Pichia pastoris, Biotechnol. Bioprocess Eng., vol. 5, pp. 275-287.*
Hang et al. (2008) A simple unstructured model-based control for efficient expression of recombinant porcine insulin precursor by Pichia pastoris, Korean J. Chem. Eng., vol. 25, pp. 1065-1069.*
Love et al. (2012) Systematic Single-Cell Analysis of Pichia pastoris Reveals Secretory Capacity Limits Productivity, PloS One, vol. 7, No. 6, pp. 1-10.*
Choi et al. (2006) Enhanced production of mouse a-amylase by feeding combined nitrogen and carbon sources in fed-batch culture of recombinant Pichia pastoris, Process Biochem., vol. 41, pp. 390-397.*
"International Application Serial No. PCT/IB2014/058171, International Preliminary Report on Patentability dated Jul. 23, 2015", 15 pgs.
"International Application Serial No. PCT/IB2014/058171, International Search Report dated Apr. 22, 2014", 8 pgs.
"International Application Serial No. PCT/IB2014/058171, Written Opinion dated Apr. 22, 2014", 13 pgs.
Amazile, B. R. A. Maria, et al., "A comparative study of effects of soy and corn flours on the evolution of alcohol fermentation in successive batches", Journal of Chemical Technology and Biotechnology, 59(2), (Feb. 1994), 171-179.
Jahic, Mehmedalija, "Process techniques for production of recombinant proteins with Pichia pastoris.", Doctorial Thesis, Department of Biotechnology, Royal Institute of Technology, S-1091 Stockholm, Sweden, (2003), 62 pgs.
Zalai, Denes, et al., "A Dynamic Fed Batch Strategy for a Pichia Pastoris Mixed Feed System to Increase Process Understanding", Biotechnology Progress, 28(3), (2012), 878-886.

* cited by examiner

Primary Examiner — Manjunath N Rao
Assistant Examiner — Samuel W Liu
(74) Attorney, Agent, or Firm — Schwegman Lundberg & Woessner, P.A.

(57) ABSTRACT

The present disclosure relates to a comprehensive model for expression of recombinant peptides by *Pichia pastoris*. The model uses an easily controllable variable called 'critical nutrient ratio' for obtaining a right balance between product synthesis and it's degradation during the fermentation process. The extra cellular concentration of precursor could be increased by about 10 folds and the degradation constants could be reduced by about 10-20 folds for intracellular and extracellular cases respectively by controlling critical nutrient ratio and addition of soya flour hydrolysate and EDTA.

7 Claims, 5 Drawing Sheets

Figure 1:
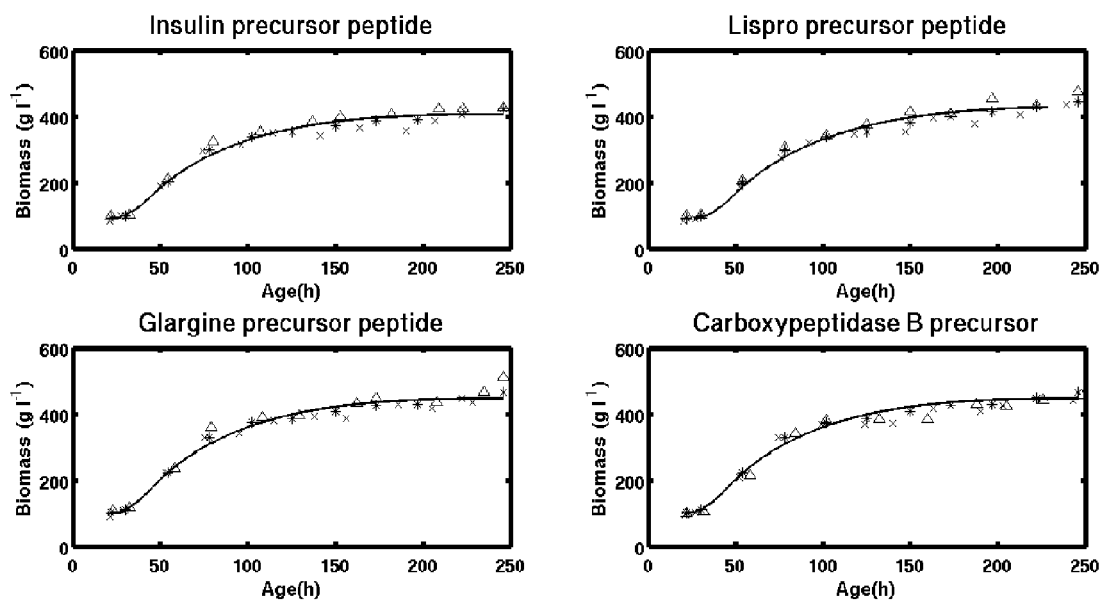

PROCESS FOR EXPRESSION OF RECOMBINANT PROTEINS IN *PICHIA PASTORIS* USING A FED BATCH MODEL

PRIORITY APPLICATIONS

This application is a U.S. National Stage Filing under 35 U.S.C. 371 from International Application No. PCT/IB2014/058171, filed on 10 Jan. 2014, and published as WO2014/108856 on 17 Jul. 2014, which claims the benefit under 35 U.S.C. 119 to Indian Application No. 137/CHE/2013, filed on 10 Jan. 2013; which applications and publication are incorporated herein by reference in their entirety.

TECHNICAL FIELD

The present disclosure relates to a comprehensive model for expression of recombinant peptides by *Pichia pastoris*. The model is structured on the lines of intracellular synthesis rate, intracellular degradation rate, intracellular accumulation, secretion, extracellular degradation rate and extracellular accumulation rate. The model uses an easily controllable variable called 'critical nutrient ratio' for obtaining a right balance between product synthesis and it's degradation during the fermentation process. The extra cellular concentration of precursor could be increased by about 10 folds and the degradation constants could be reduced by about 10-20 folds for intracellular and extracellular cases respectively by controlling critical nutrient ratio and addition of soya flour hydrolysate and EDTA.

BACKGROUND AND PRIOR ART OF THE DISCLOSURE

*Pichia pastoris*, a fast growing microbe, though easily cultivable to high cell densities, has a major drawback of relatively lower specific productivity (Porro et al., 2011). The disadvantages associated with the low productivity of the prior art have been remedied in the instant disclosure.

Robustness in the microbial process designed was introduced by using critical nutrient ratio (CNR) of two important nutrients (Tiwari et al., 2012) as a control variable for key metabolic variables like activity of a centrally important regulatory enzyme—phosphofructokinase, oxygen uptake rate as well as specific productivity. As CNR is a general parameter, it is likely to influence synthesis of degrading enzymes and transporter enzymes, just as it affects productivity of the main product.

Modeling and measuring intracellular fluxes of secreted recombinant protein in *Pichia pastoris* with a novel 34S labeling by Martin Pfeffer et al. characterizes intracellular protein formation, degradation and secretion under a steady state condition. Apart from limitation of chemostat mode of fermentation, their study is also limited to use of limiting substrate methanol instead of using critical nutrient ratio (CNR). Further, their study does not consider the losses due to extracellular degradation and hence ignores a vital aspect of protein dynamics during expression.

Hence, there exists a need in the art to include more relevant parameters in the process design space for manufacturing of recombinant peptides. In the present disclosure we have disclosed use of CNR to regulate synthesis, intracellular and extracellular degradation, secretion of recombinant peptide expressed in fed-batch mode.

STATEMENT OF THE DISCLOSURE

Accordingly, the present disclosure relates to a process of improving the expression of insulin analogue by using CNR of residual carbon to residual nitrogen nutrients in the broth as an effective tool for controlling microbial dynamics for the overall peptide biosynthesis during fermentation and explicitly improving the poor expression levels of Insulin analogue precursor in *P. pastoris* fed batch process. The present disclosure demonstrates the control of critical nutrient ratio (CNR), use of protease inhibitors like soya flour hydro lysate, urea and metalloprotease inhibitors for improved productivity of heterologous peptides and proteins like Carboxy peptidase B, Insulin and its analog using methanol inducible expression system in *Pichia Pastoris* by incorporating mathematical model for intra and extracellular product accumulation, degradation and synthesis.

BRIEF DESCRIPTION OF THE ACCOMPANYING FIGURES

The features of the present disclosure will become more fully apparent from the following description taken in conjunction with the accompanying figures. Understanding that the figures depict only several embodiments in accordance with the disclosure and are therefore, not to be considered limiting of its scope, the disclosure will be described with additional specificity and detail through use of the accompanying figures:

FIG. 1: shows actual (markers) and model fitted (solid line) profile of biomass concentration during three control fed batch runs of Insulin precursor peptide, Lispro precursor peptide, Glargine precursor peptide and Carboxypeptidase B precursor.

Figure 2:
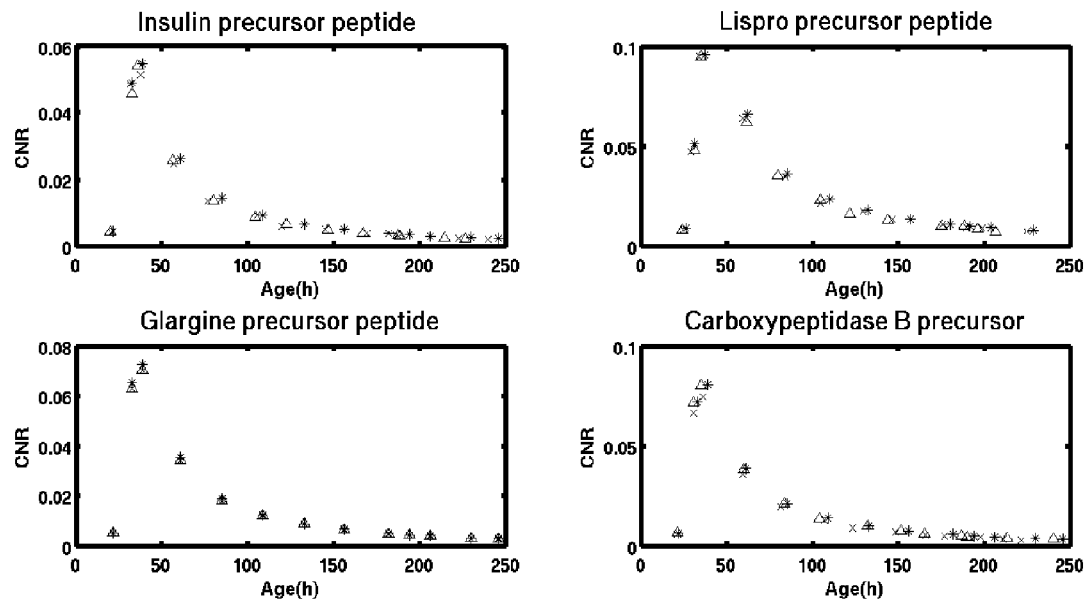

FIG. 2: shows actual (markers) profile of critical nutrient ratio (methanol to ammonia) during three control fed batch runs of Insulin precursor peptide, Lispro precursor peptide, Glargine precursor peptide and Carboxypeptidase B precursor.

Figure 3:
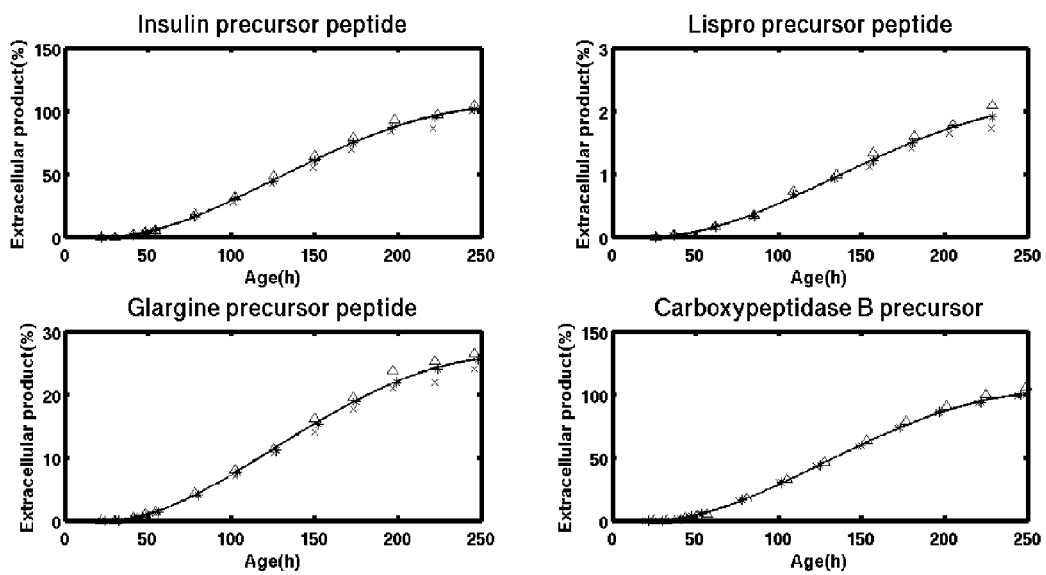

FIG. 3: shows actual (markers) and model fitted (solid line) profile of extracellular product concentration during three control fed batch runs of Insulin precursor peptide, Lispro precursor peptide, Glargine precursor peptide and Carboxypeptidase B precursor, Insulin precursor peptide and Carboxy peptidase B precursor are considered 100% in control case while Glargine precursor peptide and Lispro precursor peptide are considered as percentage with reference of Insulin precursor peptide.

Figure 4:
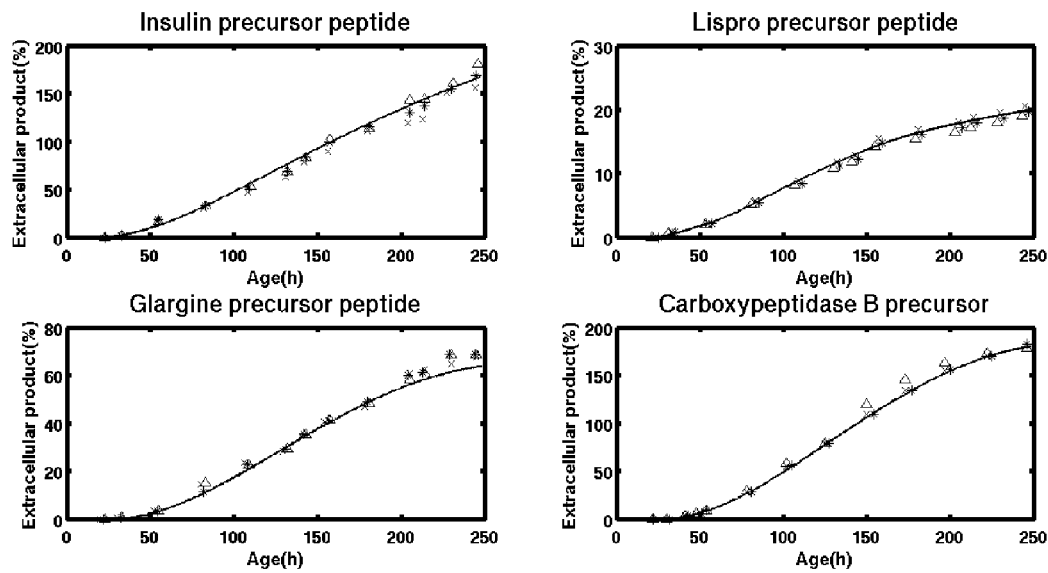

FIG. 4: shows actual (markers) and model fitted (solid line) profile of extracellular product concentration during three fed batch runs of Insulin precursor peptide, Lispro precursor peptide, Glargine precursor peptide and Carboxypeptidase B precursor with optimized critical nutrient ratio, Insulin precursor peptide Glargine precursor peptide and Lispro precursor peptide are compared with 100% in control case of Insulin precursor peptide while Carboxy peptidase B is compared with its control case extracellular expression.

Figure 5:
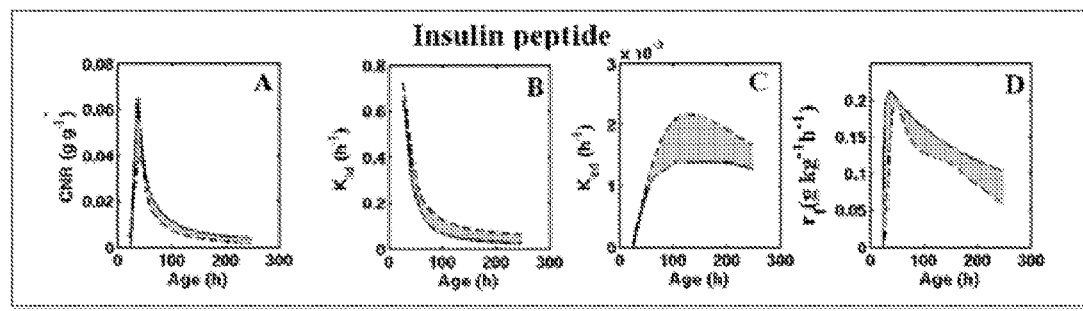

FIG. 5: shows control batch (dashed line); batch with optimum Critical nutrient ratio (solid line) for Insulin.

Figure 6:
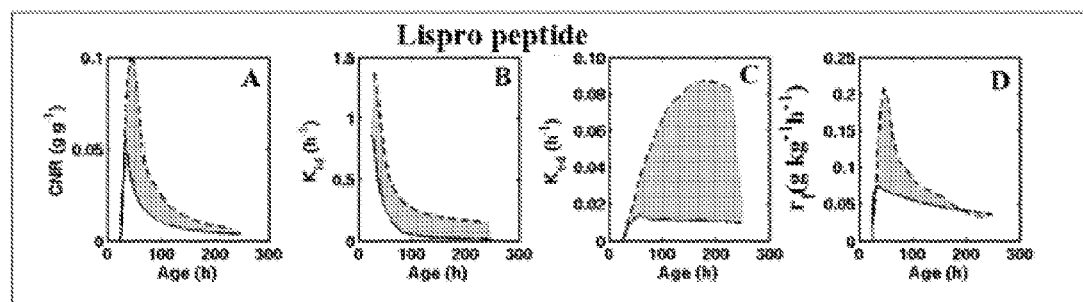

FIG. 6: shows control batch (dashed line); batch with optimum Critical nutrient ratio (solid line) for Lispro.

Figure 7:
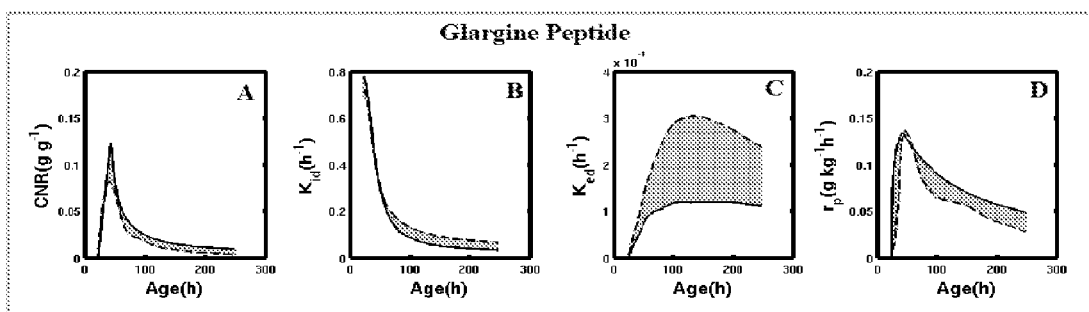

FIG. 7: shows control batch (dashed line); batch with optimum Critical nutrient ratio (solid line) for Glargine.

Figure 8:
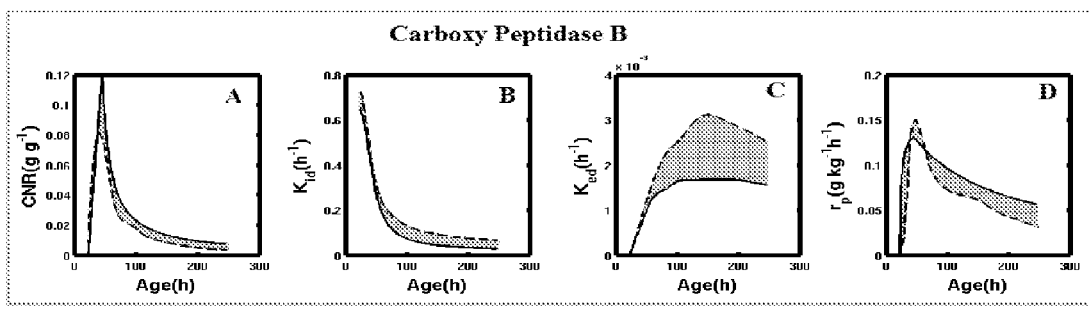

FIG. 8: shows control batch (dashed line); batch with optimum Critical nutrient ratio (solid line) for Carboxypeptidase B.

Figure 9:
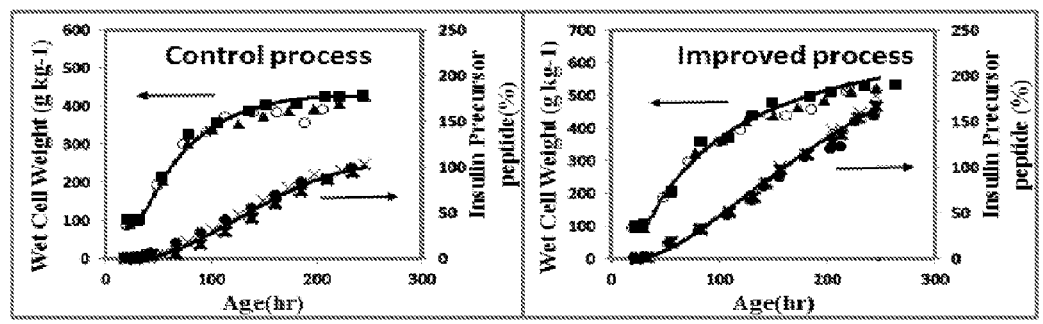

FIG. 9: shows improvements in extracellular accumulation of insulin precursor peptide, solid line simulated and marker for measured values.

Figure 10:
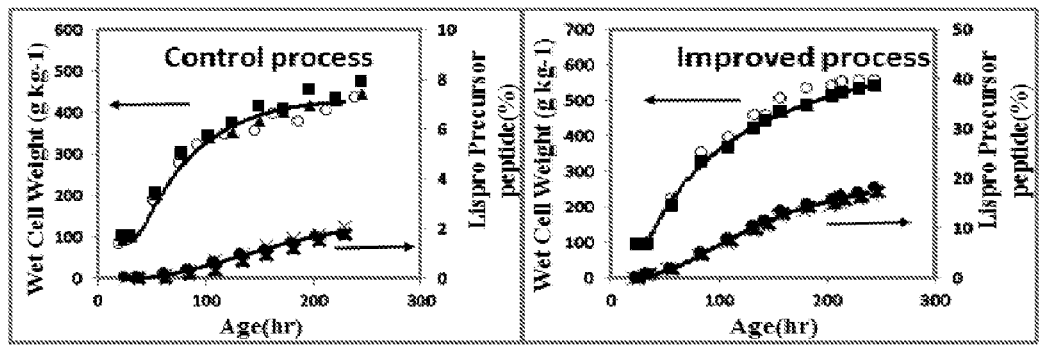

FIG. 10: shows improvements in extracellular accumulation of Lispro precursor peptide, solid line simulated and marker for measured values.

Figure 11:
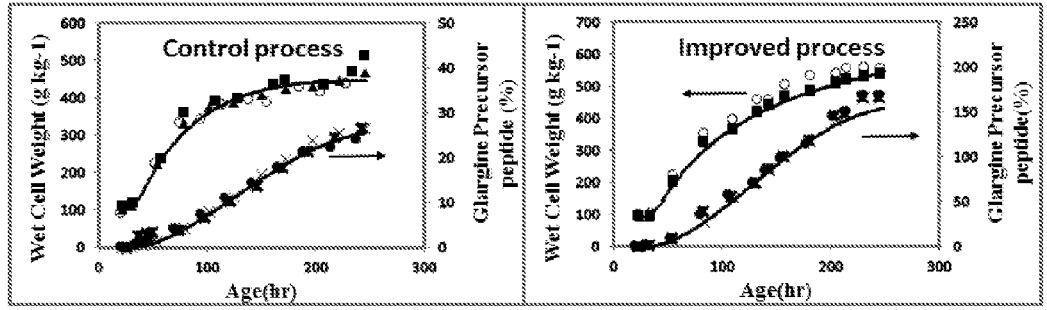

FIG. 11: shows improvements in extracellular accumulation of Glargine precursor peptide, solid line simulated and marker for measured values.

Figure 12:
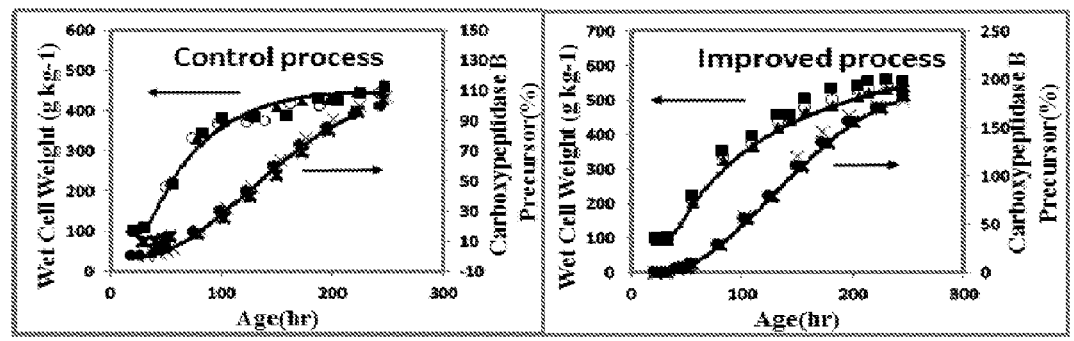

FIG. 12: shows improvements in extracellular accumulation of Carboxy peptidase B protease, solid line simulated and marker for measured values.

DETAILED DESCRIPTION OF THE DISCLOSURE

*P. pastoris* strains are used for production of the respective single chain peptide for insulin peptide, Insulin Lispro peptide, Insulin Glargine peptide and Carboxypeptidase B enzyme. The designed peptides of Insulin analogs are similar except for the reversal in positioning of proline and lysine at B28 and B29 positions respectively for Lispro peptide and the porcine Carboxypeptidase B is cloned in *Pichia pastoris*. The expression involved use of a tightly regulated alcohol oxidase enzyme (AOX) promoter which is integrated with the host genome using vector pPIC9K. The clones selected on Sigma's yeast nitrogen base (YNB) agar plate have resistance to 2 mg of G418. The culture propagated in YNB medium is used for preparing glycerol vials that were eventually kept at −70° C. freezer for long term storage. To inoculate a seed flask, contents of 1 mL glycerol vial were thawed and transferred to 50 mL of MGY broth (10 g L$^{-1}$ glycerol and 0.004 g L$^{-1}$ biotin, and YNB at 1.5% v v$^{-1}$) in 250 mL conical flask and shaken at 230 rpm and 30° C. for 24 h. Subsequently, well grown culture (OD600 nm >15) is used at approximately 10% v v$^{-1}$ to inoculate 2000 mL inoculum flasks containing about 500 mL of MGY media. The inoculum flasks are shaken at 230 rpm and 30° C. for 24 h. The broth from inoculum flask is transferred to 10 L of pre-sterilized production medium in a 50 L fermentor. The standard or control process is adapted from protocols described for *Pichia* fed batch process. (http://tools.invitrogen.com/content/sfs/manuals/pichiaferm_prot.pdf).

The production medium is sterilized at low pH of about 2.0 units by heating at 121° C. for 1 h. Post sterilization, nitrogen source is provided by adjusting the pH to 5.0 using filter sterilized ammonium sulphate in the concentration range of about 1 g/l to about 5 g/l. The end of batch phase is indicated by a noticeable rise in DO (Dissolved Oxygen) from <25% to as high as 100%. Subsequently; induction is initiated by starting methanol feeding at a rate of 1 g L$^{-1}$ h$^{-1}$. The feed rate of methanol is gradually increased up to about 10 g L$^{-1}$ h$^{-1}$. Methanol, is used not only as inducer but also as carbon and energy source is throughout maintained in the concentration of less than or equal to about 5 g/l, preferably at less than about 0.5 g L$^{-1}$. During the entire methanol fed batch phase, a pre-sterilized concentrated stock solution of YEP (5% w v$^{-1}$ yeast extract, 10% w v$^{-1}$ soya peptone) is fed at a fixed rate of 1 g L$^{-1}$ h$^{-1}$. Foam control is managed with the addition of antifoam structol J673. The entire fed batch process is run with the help of DO spike method, i.e., the time taken to observe a steep rise in DO immediately after stoppage of methanol feed, indirectly represented the accumulation of methanol in the broth. The accumulation time is strictly controlled at less than 1 minute and the accumulation timings are correlated with the methanol content in the broth. Samples, withdrawn every 24 hours after start of induction are analyzed for wet cell weight % (WCW), pH, peptide content (%), degradation rate for intra and extracellular product. The methanol, urea and ammonia content in supernatant is measured every 4-8 hours throughout the batch.

The present disclosure is in relation to a process of improvement in expression of recombinant peptides using a fed batch model dynamically structured with peptide synthesis, secretion and degradation.

The improved process is attained by running the batches in control fashion except control of critical nutrient ratio as suggested by model and controlling it by feeding Ammonium sulphate (70% w/v), Methanol (94% v/v_) and Urea (50% w/w) while Soya flour hydrolysate (16% w/v) and EDTA (16% w/v) for controlling protein degradation as required from degradation profile of the products.

In an embodiment of the present disclosure, CNR is defined by the ratio of carbon:nitrogen, a fractional/decimal value of which falls in the range of about 0.01 to 0.15. Further, the concentration of methanol employed in the instant invention is less than or equal to about 5 g/l, and the concentration of ammonium hydroxide employed is in the range of about 1 g/l to about 5 g/l.

In another embodiment of the present disclosure, the extra cellular concentration of precursor increased by about 10 folds and the degradation constants reduced by about 10-20 folds for intracellular and extracellular cases respectively.

In yet another embodiment of the present disclosure, the difference between the control process and the process of the instant invention is in the feeding profile of methanol and addition of ammonium sulphate. In the improved process of the instant invention, the feeding profile of Methanol is calculated from the model (control process) and Ammonium sulphate is used to control CNR.

Fed-Batch Dynamic Model

Precursor Mass Balance on Total Biomass as a System Boundary $$\text{Rate of formation} - \text{Rate of degradation} - \text{Rate of secretion} = \text{Rate of accumulation} \quad (1)$$

$$X*r_f - X*r_{id} - X*r_s = \frac{d(p_i*X)}{dt} \quad (2)$$

$$r_f = r_{id} + r_s + p_i*\mu + \frac{d(p_i)}{dt} \quad (3)$$

Where specific growth rate is defined as $\mu = \frac{1}{X}*\frac{d(X)}{dt}$ (4)

$p_i$ is the intracellular concentration of precursor in grams per kg of biomass; X is the total biomass in Kg; $r_f$, $r_{id}$ and $r_s$ represent the specific peptide formation rate, degradation rate and secretion rate respectively in g kg-1h-1.

Precursor Mass Balance on Cell Free Supernatant as a System Boundary $$r_s*X = r_{ed} + \frac{d(P_e)}{dt} \quad (5)$$

$$\frac{d(p_i)}{dt} + \mu*p_i + r_{id} + \left(r_{ed} + \frac{d(P_e)}{dt}\right)*\frac{1}{X_o*e^{\mu t}} - r_f = 0 \quad (6)$$

Where, $r_{ed}$ represents the extracellular degradation rate in g h-1; $P_e$ represents total extracellular product in grams. The various terms in the above equation are subsequently expanded:

Synthesis Rate ($r_f$) and Degradation Rates ($r_{id}$ & $r_{ed}$)

As the product gene is placed next to the AOX promoter, it is assumed that activity of synthesis enzymes would be proportional to the activity of induced AOX. The AOX activity in-turn depends upon the methanol as its substrate. Further, as the methanol uptake is found to be adversely affected by the concentration of another key nutrient in fermentation—ammonia, a correction is introduced in terms of CNR of methanol to ammonia. Thus, peptide synthesis rate is modeled using saturation kinetics as follows:

$$r_f = k_f*E_{AOX}*\frac{CNR}{K_{Mf}+CNR} = r_{fmax}*\frac{CNR}{K_{Mf}+CNR} \quad (7)$$

Where $k_f$ is a synthesis constant in grams of peptide synthesized per unit of AOX synthesized per h; $E_{AOX}$ represents AOX in units per gram of biomass; CNR is dynamically calculated as the ratio of methanol concentration to that of ammonia concentration in the broth; $k_{Mf}$ is the affinity constant. As AOX is a strong promoter (Zhang et al., 2000), the term '$E_{AOX}$' is replaced with a steady state value $r_{fmax}$. As reported (Bibila & Flickinger, 1991; Whitely et al., 1997; Belle et al., 2006), the actual degradation data showed first order kinetics and hence was modeled as shown below:

$$r_{id} = K_{id} * p_i \quad (8)$$

$$r_{ed} = K_{ed} * P_e \quad (9)$$

$$P_e = \frac{V*(1000-x)*p_e}{1000} \quad (10)$$

Where $K_{id}$, $K_{ed}$ are the time dependent first order rate constants in h-1; V is the broth volume in Liters; x and $p_e$ are biomass concentration and extracellular product concentration in g L-1.

Degradation Constants ($K_{id}$ & $K_{ed}$)

To explain the observed variations in the degradation constants across the batch, the dynamic behavior in terms of protease productivity and release of proteases from the cells is modelled in the instant invention. Being a general parameter, CNR is expected to affect the productivity of proteases just as it is hypothesized to affect synthesis of peptide. The cumulative impact of CNR, a metal ion chelator (I1) and a vegetable hydrolysate (I2) on the protease activity is incorporated as follows:

$$K_{id} = kpid * E_i * \left(\frac{k_{I1}}{k_{I1}+I_1}\right) * \left(\frac{k_{I2}}{k_{I2}+I_2}\right) \quad (11)$$

$$K_{ed} = kped * E_e * \left(\frac{k_{I1}}{k_{I1}+I_1}\right) * \left(\frac{k_{I2}}{k_{I2}+I_2}\right) \quad (12)$$

Where kpid and kped are the molecule specific degradation constants in grams of peptide degraded per unit activity per h; $k_{I1}$ and $k_{I2}$ are respective inhibition constants as determined from the inhibition study done on broth samples; The productivity of $E_i$, the net intracellular protease in units per gram of biomass is modeled as described in equation (7):

$$\frac{1}{X} * \frac{d(E_i * X)}{dt} = r_{idmax} * \frac{CNR}{K_{Mid}+CNR} \quad (13)$$

$$\frac{d(E_i)}{dt} + E_i * \mu - r_{idmax} * \frac{CNR}{K_{Mid}+CNR} = 0 \quad (14)$$

Where $r_{idmax}$ denotes the maximum productivity of proteases in units per gram of biomass per h; $k_{Mid}$ is the affinity constant; Ee is extracellular protease concentration in units per gram of supernatant. The dynamic release of proteases from biomass is modeled as follows:

$$\frac{d\left(V*\frac{(1000-x)}{1000}*E_e\right)}{dt} = \left\{(k_{es}*X) + \frac{d((1-v)*X)}{dt}*E_i\right\} \quad (15)$$

Where, $k_{es}$ is the rate of continuous release of proteases from cells in units per gram of biomass per h; x is the concentration of biomass in g L-1, v denotes actual fractional viability of the cells.

Specific Growth Rate (t) and Intracellular Secretion Rate ($r_s$)

As the activity of regulatory enzymes such as phosphofructokinase (Voet & Voet, 2004) is affected not just by substrate (Tiwari et al., 2012; Habison et al., 1983; Buckwitz et al., 1990), it was necessary to correct the amount of carbon nutrient that would bind to enzyme in presence of nitrogen nutrient. This is achieved by using CNR in the Monod type of model as it would confine the amount of carbon nutrient that can bind to the centrally important enzyme and hence affect the specific growth rate as follows:

$$\mu = \frac{\mu_m * CNR}{(K_{xs}+CNR)} \quad (16)$$

The rate of secretion of peptides ($r_s$), being an enzyme linked process (Kjeldsen, 2000) is also modeled as follows:

$$r_s = \frac{r_{smax} * p_i}{(K_{ps}+p_i)} = \frac{(k_{cat}*E_t)*p_i}{(K_{ps}+p_i)} \quad (17)$$

Where $E_t$ represents transporter enzymes in units per gram of biomass; $k_{cat}$ is the constant for conversion of Et–$p_i$ complex to $p_e$, in grams of peptide per unit activity per h. The productivity of $E_t$ was modeled as described in equation (14):

$$\frac{d(E_t)}{dt} + E_t * \mu - r_{tmax} * \frac{CNR}{K_{Mt}+CNR} = 0 \quad (18)$$

Where $r_{tmax}$ denotes the maximum productivity of Et; $k_{Mt}$ is the affinity constant. In addition, the following mass balance equations are used for the fermentor as a system:

$$V = V_o + \int F * dt \quad (19)$$

$$F = F_{carbon} + F_{nitrogen} + F_{I1} + F_{I2} \quad (20)$$

Where F denotes feed rate in Liters per hour; Vo is the initial volume in Liters.

Working with the Model

Data from three control fermentation runs of each peptide is used to obtain values of various constants in the model by minimizing the error between model outputs with respect to experimental data. The constants KI1 and KI2 are determined from actual in-vitro degradation studies using I1 and I2 separately on supernatant samples from control fermentation runs. The model thus obtained showed $p_e$ as a function of easily measurable and controlled variables: CNR, I1 and I2. While the ramp up of concentrations of I1 and I2 upto the respective maximum concentrations are determined from actual experimental studies with due considerations for growth and substrate uptake. The optimum profile of CNR as a control variable is determined by maximizing the objective function of rate of change in $P_e$ every hour from the start of induction to the end of fermentation.

Several constraints are imposed to arrive at a solution. Some of the examples are given below:

A constraint is imposed by experimentally determined maximum heat and oxygen transfer rate in the bioreactor, implicit in the maximum amount of biomass formed per hour (<100 g h$^{-1}$). This constraint is aimed at determining CNR optimum for specific growth rate, the maximum possible rate of peptide formation as derived from equation (17):

$$NR \leq \frac{100 * K_{xs}}{(\mu_m * X - 100)};$$

Additional constraint on CNR is imposed in order to reduce intracellular degradation rate in particular for the unstable and 'difficult to express' Lipsro peptide, by equating target $K_{id}$ to the intracellular degradation rate constant of relatively stable insulin peptide as determined by control process run. Further, another process constraint is implemented on maximum secretion rate, based on reported (Werten et al., 1999) highest extracellular peptide accumulation of about 15 g L-1, which is higher than the expression levels of insulin peptide as well as lispro peptide. Hence, it is assumed that secretion is not a bottleneck upto 15 g $L^{-1}$ of extracellular peptide. Thus obtained profile of CNR is verified for impact on $p_e$ by actually running three batches of insulin peptide and lispro peptide, Glargine peptide and carboxypeptidase B each with optimum CNR profile.

A more complete understanding can be obtained by reference to the following specific examples, which are provided for purposes of illustration only and are not intended to limit the scope of the disclosure.

Example 1

The control processes run using above mentioned protocols adapted from Invitrogen fermentation process guidelines, gave different expression results for the insulin peptide, lispro peptide, Glargine peptide and Carboxy peptidase B protein. The profile of biomass, nutrient ratio as well as extracellular accumulation of respective peptides is shown in the FIGS. 1-3:

The overall extracellular expression of lispro precursor peptide and Glargine precursor peptide are only about 2% and 25.5% of that found for insulin peptide as shown in FIG. 3. Insulin peptide has highest expression which is considered as 100% shown in FIG. 3. Since Carboxypeptidase B precursor is different from Insulin, the maximum activity of Carboxy peptidae B precursor is considered as 100% in control batches and its profile is shown in FIG. 3. The control studies are used to study the differences not only in extracellular accumulation of these peptides, but also determine relevant constants used in the model. Subsequently, the model is used to predict optimum profile of critical nutrient ratio. The predicted profile of nutrient ratio is then verified by actual experimental runs for all the peptides.

Example 2

In order to maximize the overall extracellular accumulation of relatively stable insulin-peptide, Glargine peptide and Carboxy peptidase B, the model strategized a general increase in critical nutrient ratio represented in FIGS. 5(A), 7(A) and 8(A). As shown in the FIG. 4, the overall extracellular accumulation of insulin precursor-peptide increased from 100% to 175%, for Glargine precursor peptide the extracellular accumulation increased from 25.5% to 61.5% and for Carboxypeptidase B extracellular expression increased from 100% to 180%. The summary of increase in extracellular accumulation of Insulin Precursor peptide, Glargine Precursor peptide and Carboxypeptidase Precursor protease is shown in FIGS. 9, 11 and 12.

Example 3

In order to maximize the overall extracellular accumulation of relatively unstable Lispro-peptide, the model strategized a general decrease in critical nutrient ratio as shown in FIG. 6(A). As shown in the FIG. 10, the overall extracellular accumulation of Lispro-peptide increased by about 9 folds from 2% to 20%.

Example 4

The impact of using optimum nutrient ratio on peptide synthesis as well as degradation is evaluated and is shown in FIG. 5-8. As shown in the figure, the optimization approach increased CNR for insulin peptide, Glargine peptide and Carboxypeptidase B but reduced CNR for Lispro peptide. Resultantly, the synthesis rate of insulin peptide, Glargine peptide and carboxypeptidase B is found to increase while for Lispro peptide it is decreased. Further, the degradation constants were found to drop for all the peptides and protein. The FIG. 5-8 show impact of above changes in peptide dynamics on overall extracellular expression for insulin precursor peptide, Lispro peptide, Glargine peptide and Carboxypeptidase B. While the extracellular accumulation of insulin peptide, Glargine peptide and Carboxypeptidase B could be improved by about 38%, 140% and 180%, the corresponding improvements for Lispro peptide are about 10 folds the overall performance of insulin and analogues are summarized in FIG. 9-11. This verifies the regulatory potential of CNR to favorably influence peptide dynamics during fed-batch fermentation runs. For Lispro peptide the degradation constant is further controlled by adding EDTA and Soyaflour hydrolysate in the range of 15-20 g/l and 5-6% w/v. Since Lispro is an unstable analog as compared to other protein or peptide products of the instant invention, Soyaflour hydrolysate and EDTA are exclusively added during the process for Lispro production, while in case of other stable products Yeast extract and soya peptone are added (YEP feed).

Example 5

In order to understand the overall efficiency of expression machinery, a theoretical calculation of various expression related parameters for control as well as the improved process is done using the respective measured/predicted parameters. Table I shows 67.9% and 2.5% of the insulin precursor (IP) and Lispro precursor (LP) synthesized respectively accumulated extracellular in the respective control processes. Similarly, 79.6% and 17.4% of the Insulin precursor (IP) and Lispro precursor synthesized respectively secreted in control process. The significant differences between IP and LP, are attributed to higher intracellular and extracellular degradation of LP at 80.6% of the LP synthesized and 85.7% of LP secreted as against 21.6% of the IP synthesized and 14.7% of IP secreted. In addition, the overall synthesis of LP is also lesser at 51.8% of that of IP. The approach reduced intracellular degradation of LP to 21.9% of the peptide synthesized in improved process, acceptable level based on results of stable IP in the control or improved process. However, a drop in extracellular degradation of AP from 85.7% to 50.8% in the improved process suggests scope for further reduction and might require additional optimization studies on CNR as well as additional additives. The LP accumulated extracellular as a percentage of total synthesized could be increased from 2.5% to 35.7%.

TABLE I

Overall mass balance on Insulin and Lispro peptide in the respective fed-batch fermentation

| | | Control (invitrogen) Process | | | | | | Improved process | | | | | |
|---|---|---|---|---|---|---|---|---|---|---|---|---|---|
| | Details of expression parameters | Insulin peptide | | | Lispro peptide | | | Insulin Peptide | | | Lispro peptide | | |
| S. No | (measured calculated predicted) | (%)$^a$ | (%)$^b$ | (%)$^c$ | (%)$^a$ | (%)$^b$ | (%)$^c$ | (%)$^a$ | (%)$^b$ | (%)$^c$ | (%)$^a$ | (%)$^b$ | (%)$^c$ |
| 1 | Peptide accumulated extracellular | 67.9 | 85.3 | 67.9 | 1.3 | 14.4 | 2.5 | 93.7 | 90.3 | 73.2 | 17.1 | 49.3 | 35.7 |
| 2 | Peptide degraded extracellular | 11.7 | 14.7 | 11.7 | 7.7 | 85.6 | 14.9 | 10.1 | 9.7 | 7.9 | 17.6 | 50.7 | 36.9 |
| 3 | Peptide actully secreted(1 + 2) | 79.6 | 100.0 | 79.6 | 9.0 | 100.0 | 17.4 | 103.8 | 100.0 | 81.1 | 34.7 | 100.0 | 72.6 |
| 4 | Intracellular peptide retained | 1.4 | | 1.4 | 1.3 | | 2.5 | 3.4 | | 2.6 | 2.4 | | 5.1 |
| 5 | Intracellular peptide degraded | 21.6 | | 21.6 | 41.8 | | 80.7 | 20.8 | | 16.3 | 10.5 | | 21.9 |
| 6 | Peptide synthesized | 100 | | 100 | 51.8 | | 100.0 | 128 | | 100 | 47.7 | | 100.0 |
| 7 | Peptide available for secretion(6-5-4) | 77 | | 77 | 8.7 | | 16.8 | 103.8 | | 81.1 | 34.8 | | 73.0 |
| 8 | Deifference between 3& 7 | 2.5 | | 2.5 | 2.5 | | 0.6 | 0 | | 0 | 0.1 | | 0.4 |

$^a$% calculation relative to the total insulin peptide synthesized in the control case;
$^b$% calculation based on measured extracellular peptide as well as extracellular degradation;
$^c$% calculation relative to the total peptide synthesized in the respective case

Example 6

In order to understand the overall efficiency of expression machinery, a theoretical calculation of various expression related parameters for control as well as the improved process is done using the respective measured/predicted parameters. Table II shows 67.9% and 17.3% of the insulin precursor (IP) and Glargine precursor (GP) synthesized respectively accumulated extracellular in the respective control processes. Similarly, 79.6% and 48% of the Insulin precursor (IP) and Glargine precursor synthesized respectively secreted in control process. The significant differences between IP and GP, are attributed to higher intracellular and extracellular degradation of GP at 47% of the GP synthesized and 48% of GP secreted as against 21.6% of the IP synthesized and 14.7% of IP secreted. In addition, the overall synthesis of GP is equivalent to 95% of that of IP. The approach reduced intracellular degradation of GP to 36.4% of the peptide synthesized in improved process, acceptable level based on results of stable IP in the control or improved process. However, a drop in extracellular degradation of GP from 32.3.7% to 23.3% in the improved process suggests scope for further reduction and might require additional optimization studies on CNR as well as additional additives. The GP accumulated extracellular as a percentage of total synthesized could be increased from 18.2% to 37.9%.

TABLE II

Overall mass balance on Insulin and Glargine peptide in the respective fed-batch fermentations

| | | Control (invitrogen) Process | | | | | | Improved process | | | | | |
|---|---|---|---|---|---|---|---|---|---|---|---|---|---|
| | Details of expression parameters | Insulin peptide | | | Glargine peptide | | | Insulin Peptide | | | Glargine peptide | | |
| S. No | (measured calculated predicted) | (%)$^a$ | (%)$^b$ | (%)$^c$ | (%)$^a$ | (%)$^b$ | (%)$^c$ | (%)$^a$ | (%)$^b$ | (%)$^c$ | (%)$^a$ | (%)$^b$ | (%)$^c$ |
| 1 | Peptide accumulated extracellular | 67.9 | 85.3 | 67.9 | 17.3 | 36.0 | 18.2 | 93.7 | 90.3 | 73.2 | 41.7 | 61.9 | 37.9 |
| 2 | Peptide degraded extracellular | 11.7 | 14.7 | 11.7 | 30.7 | 64.0 | 32.3 | 10.1 | 9.7 | 7.9 | 25.6 | 38.1 | 23.3 |
| 3 | Peptide actually secreted(1 + 2) | 79.6 | 100.0 | 79.6 | 48.0 | 100.0 | 50.5 | 103.8 | 100.0 | 81.1 | 67.3 | 100.0 | 61.1 |
| 4 | Intracellular peptide retained | 1.4 | | 1.4 | 1.5 | | 1.6 | 3.4 | | 2.6 | 2.4 | | 2.2 |
| 5 | Intracellular peptide degraded | 21.6 | | 21.6 | 45.0 | | 47.4 | 20.8 | | 16.3 | 40.0 | | 36.4 |
| 6 | Peptide synthesized | 100 | | 100 | 95.0 | | 100.0 | 128 | | 100 | 110.0 | | 100.0 |
| 7 | Peptide available for secretion(6-5-4) | 77 | | 77 | 48.5 | | 51.1 | 103.8 | | 81.1 | 67.6 | | 61.5 |
| 8 | Deifference between 3& 7 | 2.5 | | 2.5 | 0.5 | | 0.5 | 0 | | 0 | 0.3 | | 0.3 |

$^a$% calculation relative to the total insulin peptide synthesized in the control case;
$^b$% calculation based on measured extracellular peptide as well as extracellular degradation;
$^c$% calculation relative to the total peptide synthesized in the respective case similar to these, line total extracellular Carboxypeptidase B activity is increased from 25% to 40.9% as shown in table III.

TABLE III

Overall mass balance on Carboxy peptidase B protein in the respective fed-batch fermentations

| S. No. | Details of expression parameters (measured calculated predicted) | Control (invitrogen) Process Carboxy peptidase B | | | Improved process Carboxy peptidase B | | |
|---|---|---|---|---|---|---|---|
| | | (%)$^a$ | (%)$^b$ | (%)$^c$ | (%)$^a$ | (%)$^b$ | (%)$^c$ |
| 1 | Peptide accumulated extracellular | 25 | 50.0 | 25.0 | 45.0 | 67.2 | 40.9 |
| 2 | Peptide degraded extracellular | 25 | 50.0 | 49.1 | 22.0 | 32.8 | 20.0 |
| 3 | Peptide actully secreted(1 + 2) | 50 | 100.0 | 74.1 | 67.0 | 100.0 | 60.9 |
| 4 | Intracellular peptide retained | 2.1 | | 4.1 | 2.4 | | 2.4 |
| 5 | Intracellular peptide degraded | 47 | | 21.6 | 40.0 | | 36.4 |
| 6 | Peptide synthesized | 100 | | 100.0 | 110.0 | | 100.0 |
| 7 | Peptide available for secretion(6-5-4) | 50.9 | | 74.3 | 67.6 | | 61.2 |
| 8 | Deifference between 3& 7 | 0.9 | | 0.2 | 0.6 | | 0.3 |

$^a$% calculation relative to the total Carboxypeptidase B peptide synthesized in the control case;
$^b$% calculation based on measured extracellular peptide as well as extracellular degradation;
$^c$% calculation relative to the total peptide synthesized in the respective case

We claim:

1. A process for the expression of a recombinant protein in *Pichia pastoris* comprising the steps of fed batch culturing of the *Pichia pastoris* in a medium with a carbon: nitrogen ratio of about 0.01 to 0.15 to increase the recombinant protein synthesis and adding soya flour hydrolysate and EDTA to the medium so as to reduce protein degradation by reducing a degradation constant compared to a control in which said expression is performed in the absence of said carbon:nitrogen ratio and said adding step, wherein the recombinant protein is selected from the group consisting of lispro (fast acting insulin) precursor peptide, an insulin analogue, glargine (long acting insulin) and carboxypeptidase.

2. The process as claimed in claim 1, wherein the process reduces intracellular and extracellular protease activity by decreasing protease synthesis rate and release of the recombinant protein into the medium.

3. The process as claimed in claim 1, where the EDTA is added at a concentration of 15-20 g/l and the soya flour hydrolysate is added at a concentration range of 5-6% w/v.

4. The process as claimed in claim 1, wherein the extracellular concentration of the lispro precursor peptide is increased by about 10-fold compared to the control and the degradation constants for the lispro precursor peptide are reduced by about 10-fold to 20-fold compared to the control.

5. The process as claimed in claim 1, wherein the extracellular concentration of the insulin analogue is increased by about 1.5-fold compared to the control while the degradation constants for the insulin analogue are reduced by 1.4-fold compared to the control.

6. The process as claimed in claim 1, wherein extracellular concentration of the glargine is increased by about 2.4-fold compared to the control while the degradation constants for the glargine are reduced by 3-fold compared to the control.

7. The process as claimed in claim 1, wherein the extracellular concentration of carboxypeptidase is increased by about 1.8-fold compared to the control while the degradation constants for carboxypeptidase are reduced by about 1.9-fold compared to the control.

* * * * *